United States Patent
Ryu et al.

(10) Patent No.: US 9,572,620 B2
(45) Date of Patent: Feb. 21, 2017

(54) SYSTEM AND METHOD FOR TREATING ARRHYTHMIAS IN THE HEART USING INFORMATION OBTAINED FROM HEART WALL MOTION

(76) Inventors: Kyungmoo Ryu, Palmdale, CA (US); Thao T. Ngo, Shakopee, MN (US); Euljoon Park, Valencia, CA (US); Stuart Rosenberg, Castaic, CA (US); Allen Keel, San Francisco, CA (US); Wenbo Hou, Lancaster, CA (US); Steve Koh, South Pasadena, CA (US); Kjell Noren, Solna (SE); Michael Yang, Thousand Oaks, CA (US)

( * ) Notice: Subject to any disclaimer, the term of this patent is extended or adjusted under 35 U.S.C. 154(b) by 1268 days.

(21) Appl. No.: 12/980,586

(22) Filed: Dec. 29, 2010

(65) Prior Publication Data
US 2012/0172867 A1 Jul. 5, 2012

(51) Int. Cl.
*A61B 18/12* (2006.01)
*A61B 5/11* (2006.01)
(Continued)

(52) U.S. Cl.
CPC ......... *A61B 18/1206* (2013.01); *A61B 5/1107* (2013.01); *A61B 18/082* (2013.01);
(Continued)

(58) Field of Classification Search
CPC  A61B 2018/00351; A61B 2018/00357; A61B 2018/00563; A61B 2018/00642;
(Continued)

(56) References Cited

U.S. PATENT DOCUMENTS

| 6,405,067 B1 * | 6/2002 | Mest .................. A61B 18/1492 600/374 |
| 7,263,397 B2 | 8/2007 | Hauck et al. |

(Continued)

FOREIGN PATENT DOCUMENTS

WO   WO2010/131178   * 11/2010 ............... A61B 5/00

OTHER PUBLICATIONS

Ren, Jian-Fang et al., "Increased Intensity of Anticoagulation May Reduce Risk of Thrombus During Atrial Fibrillation Ablation Procedures in Patients With Spontaneous Echo Contrast," 16 Journal of Cardiovascular Electrophysiology pp. 474-477 (May 2005).
(Continued)

*Primary Examiner* — Jaymi Della
(74) *Attorney, Agent, or Firm* — Dykema Gossett PLLC (57) ABSTRACT

A system and method for treating an arrhythmia in a heart are provided. The system includes an electronic control unit configured to monitor movement of one or more position sensor over a period of time. The position sensors may, for example, comprise electrodes or coils configured to generate induced voltages and currents in the presence of electromagnetic fields. The positions sensors are in contact with portions of heart tissue and changes in position are representative of motion of that tissue. The electronic control unit is further configured to generate an indicator, responsive to the movements of the sensors over the period of time, of a characteristic of the heart affected by delivery of ablation energy to heart tissue. In this manner, the effectiveness and safety of cardiac tissue ablation for treatment of the arrhythmia can be assessed and a post-ablation therapy regimen determined.

18 Claims, 6 Drawing Sheets

(51) Int. Cl.
- *A61B 18/08* (2006.01)
- *A61B 18/14* (2006.01)
- *A61B 18/20* (2006.01)
- *A61B 18/00* (2006.01)
- *A61B 18/02* (2006.01)
- *A61N 7/02* (2006.01)

(52) U.S. Cl.
CPC ........... *A61B 18/1492* (2013.01); *A61B 18/20* (2013.01); *A61B 2018/0088* (2013.01); *A61B 2018/00375* (2013.01); *A61B 2018/00577* (2013.01); *A61B 2018/00642* (2013.01); *A61B 2018/00666* (2013.01); *A61B 2018/00702* (2013.01); *A61B 2018/00726* (2013.01); *A61B 2018/00744* (2013.01); *A61B 2018/0212* (2013.01); *A61B 2034/2051* (2016.02); *A61B 2218/002* (2013.01); *A61N 7/022* (2013.01)

(58) Field of Classification Search
CPC  A61B 2018/00577; A61B 2018/00761; A61B 2018/00726; A61B 2018/00702; A61B 2018/00838; A61B 2018/00666; A61B 5/1107; A61B 5/065; A61B 5/063; A61B 19/5244; A61B 19/5259; A61B 19/5297; A61B 5/061; A61B 5/0295; A61B 2018/00744

USPC .............................. 606/34, 38; 600/347, 475
See application file for complete search history.

(56) References Cited

U.S. PATENT DOCUMENTS

| | | | |
|---|---|---|---|
| 2006/0106375 A1* | 5/2006 | Werneth et al. | 606/32 |
| 2007/0106289 A1* | 5/2007 | O'Sullivan | 606/41 |
| 2007/0123944 A1* | 5/2007 | Zdeblick | 607/17 |
| 2008/0183072 A1* | 7/2008 | Robertson et al. | 600/425 |
| 2009/0157136 A1 | 6/2009 | Yang et al. | |
| 2009/0254140 A1 | 10/2009 | Rosenberg et al. | |
| 2009/0306732 A1 | 12/2009 | Rosenberg et al. | |
| 2010/0152801 A1 | 6/2010 | Koh et al. | |
| 2010/0268059 A1 | 10/2010 | Ryu et al. | |

OTHER PUBLICATIONS

Boyd, Anita C., et al. "Differential Recovery of Regional Atrial Contraction After Restoration of Sinus Rhythm After Intraoperative Linear Radiofrequency Ablation for Atrial Fibrillation," 103 American Journal of Cardiology pp. 528-534 (2009).

* cited by examiner

FIG.5 though ablation energy delivery to the heart. In certain embodiments of the invention, the indicator may comprise an index indicative of the contractility or volume of a heart chamber or image data use by a display to generate an image of the heart. The characteristic may comprise, for example, electrical conductivity of the heart, a hemodynamic characteristic such as heart tissue velocity or blood flow velocity or a characteristic of the blood within the heart such as the existence of cavitation or a thrombus.

SYSTEM AND METHOD FOR TREATING ARRHYTHMIAS IN THE HEART USING INFORMATION OBTAINED FROM HEART WALL MOTION

BACKGROUND OF THE INVENTION a. Field of the Invention

This invention relates to a system and method for treating arrhythmias in the heart. In particular, the instant invention relates to a system and method that monitor movement of position sensors on heart tissue to generate indicators of various characteristics of the heart affected by the delivery of ablation energy.

b. Background Art

It is well known to use ablation catheters to create tissue necrosis in cardiac tissue to correct cardiac arrhythmias (including, but not limited to, atrial fibrillation, atrial flutter, atrial tachycardia and ventricular tachycardia). Arrhythmia can create a variety of dangerous conditions including irregular heart rates, loss of synchronous atrioventricular contractions and stasis of blood flow which can lead to a variety of ailments and even death. It is believed that the primary cause of many arrhythmias is stray electrical signals within one or more heart chambers. The ablation catheter imparts ablative energy (e.g., radiofrequency energy, light energy, ultrasound, or thermal (cryo or heat based) energy) to the heart tissue to create a lesion in the heart tissue. This lesion disrupts undesirable electrical pathways and thereby limits or prevents stray electrical signals that lead to arrhythmias.

Ablation therapy provides significant benefits in resolving cardiac arrhythmias. There are, however, a number of risks associated with ablation therapy including reduced contribution by atria to ventricular filling, stagnation of blood in the atria leading to a hematoma or thrombus, cavitation of blood resulting from heating during ablation which can result in creation of an embolus or thrombus, and coagulation of blood resulting from the presence of a foreign object (i.e., the ablation catheter) which can result in creation of a thrombus. For these and other reasons, it is important to monitor the impact and effectiveness of ablation therapy on cardiac tissue so that risks are minimized and the safety of a patient insured.

The inventors herein have recognized a need for a system and method for treating arrhythmias in the heart that will minimize and/or eliminate one or more of the above-identified deficiencies.

BRIEF SUMMARY OF THE INVENTION

It is desirable to provide a system and method for treating arrhythmias in the heart. In particular, it is desirable to provide a system and method that enables a clinician to determine the safety and effectiveness of ablation therapy in the treatment of cardiac arrhythmias.

A system for treating an arrhythmia in a heart in accordance with one embodiment of the present teachings includes an electronic control unit configured to monitor movement of a position sensor over a period of time. The position sensor is in contact with a first portion of tissue of the heart. In certain embodiments of the invention, the position sensor may comprise an electrode or a coil in which a voltage or current is inducted due to the presence of an electrical and/or magnetic field. The electronic control unit is further configured to generate an indicator, responsive to the movement of the position sensor over the period of time, A method for treating an arrhythmia in a heart in accordance with one embodiment of the present teachings includes the step of monitoring movement of a position sensor over a period of time. The position sensor is in contact with a first portion of tissue of the heart. The method further includes the step of delivering ablation energy to a second portion of tissue of the heart. The method further includes the step of generating an indicator, responsive to the movement of the first position sensor over the period of time, of a characteristic of the heart affected by delivery of the ablation energy.

A system and method in accordance with the present teachings are advantageous because the system and method provide an effective measure of the effectiveness of ablation therapy. In particular, the motion of the position sensors is used to infer motion of the cardiac tissue and this motion can be used to assess the impact of ablation therapy during or after administration of the therapy. For example, a lack of motion in certain tissues may indicate that an electrical pathway has been effectively severed and the treatment successful. Motion of certain tissues may also provide an indication of a change in blood flow between the atrial and ventricular chambers resulting from the ablation therapy such that an optimal pos-operative anticoagulation regimen can be determined. The inventive system and method therefore enable a clinician to better assess the efficacy and safety of ablation therapy.

The foregoing and other aspects, features, details, utilities and advantages of the present invention will be apparent from reading the following description and claims, and from reviewing the accompanying drawings.

DETAILED DESCRIPTION OF EMBODIMENTS OF THE INVENTION

Figure 1:
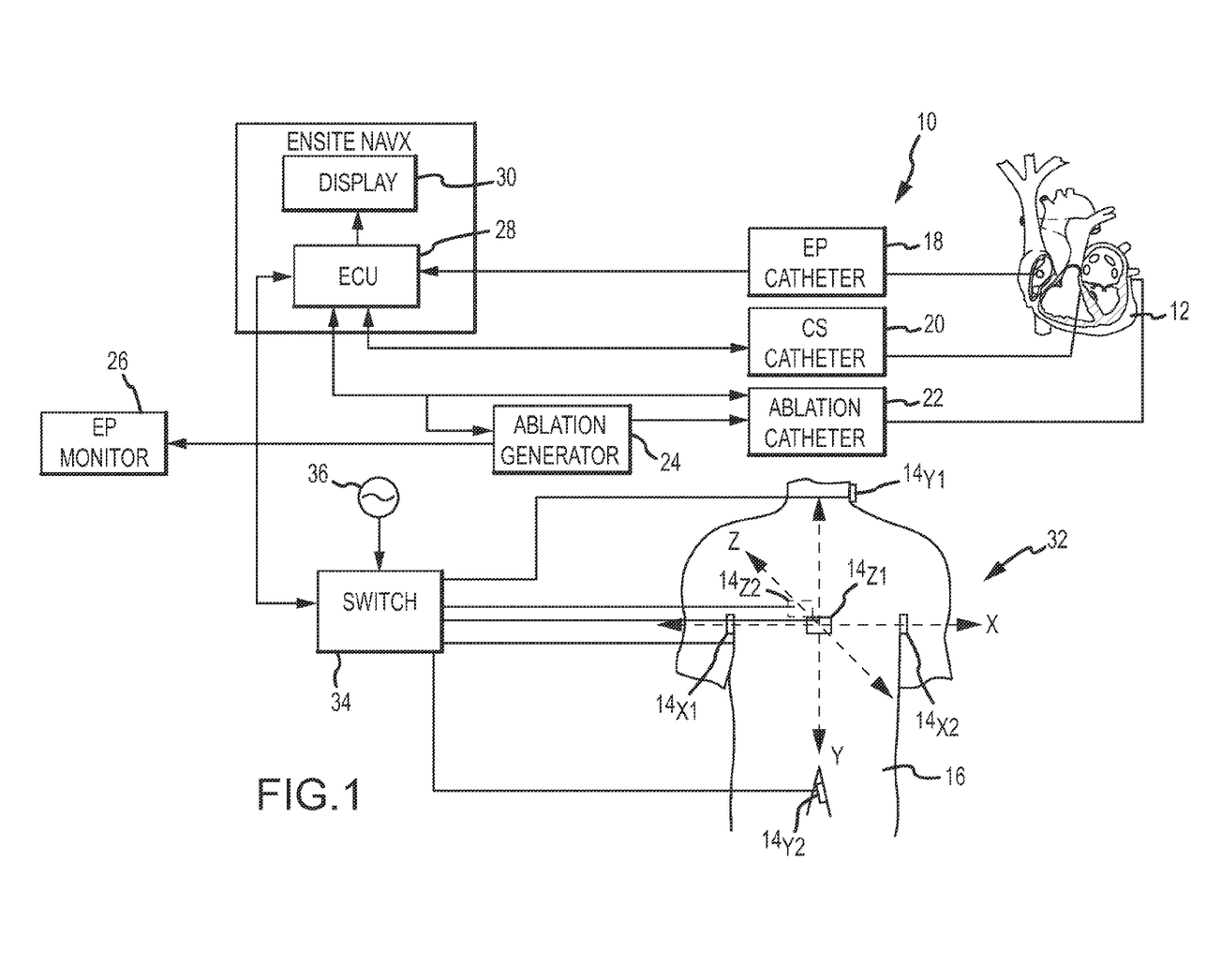
FIG. 1 is diagrammatic view of one embodiment of a system for treating an arrhythmia of the heart in accordance with the present teachings.

Referring now to the drawings wherein like reference numerals are used to identify identical components in the various views, FIG. 1 illustrates one embodiment of a system 10 for treatment of an arrhythmia of a heart 12 in accordance with the present teachings. System 10 may include a plurality of patch electrodes 14 applied to the surface of the body 16, a plurality of catheters including electrophysiological (EP) catheter 18, coronary sinus (CS) catheter 20 and ablation catheter 22, an ablation generator 24, an EP monitor 26, an electronic control unit (ECU) 28 and a display 30.

Patch electrodes 14 can generate or receive electrical signals which can be used in determining the position of catheters 18, 20, 22 within a three dimensional coordinate system 32 and to generate EP data regarding heart 12. Electrodes 14 are made from flexible, electrically conductive material and are configured for affixation to body 16 such that electrodes 14 are in electrical contact with the patient's skin. Electrodes 14 are used to create specific electric fields within body 16. As one example, electrodes $14_{X1}$, $14_{X2}$ may be placed along a first (x) axis. Similarly, electrodes $14_{Y1}$, $14_{Y2}$ may be placed along a second (y) axis and electrodes $14_{Z1}$, $14_{Z2}$ may be placed along a third (z) axis. Alternative electrode placements will create alternate fields. For example, three electrodes 14 may be placed underneath the patient (not shown) and create a field with an electrode on a catheter on the patient's chest (not shown). Each of the electrodes 14 may be coupled to a multiplex switch 34. ECU 28 is configured through appropriate software to provide control signals to switch 34 and thereby sequentially couple pairs of electrodes 14 to a signal generator 36. Excitation of each pair of electrodes 14 generates an electric field within body 16 and within an area of interest such as heart 12. Voltage levels at non-excited electrodes 14 are filtered and converted and provided to ECU 28 for use as reference values. In addition, or alternatively, an additional patch electrode 14 may be located on the surface of the body (e.g., near the navel) to act as a reference.

Catheters 18, 20, 22 are each provided for specific purposes as described hereinbelow. It should be understood, however, that catheters 18, 20, 22 are exemplary and that aspects of a system and method in accordance with the present teachings can be practiced using a variety of conventional catheters. In general, catheters such as catheters 18, 20, 22 used with system 10 may be used to allow removal of fluids from body 16 or injection of fluids and medicine into body 16 and may further provide a means for transporting surgical tools or instruments within body 16 including those used for electrophysiological mapping and tissue ablation. Catheters 18, 20, 22 may be formed from conventional materials such as polyurethane. Catheters 18, 20, 22 are tubular and deformable and may be guided within body 16 by a guide wire or other means known in the art. The catheters 18, 20, 22 have a proximal end and a distal end. As used herein, "distal" refers to an end of catheter 18, 20, 22 that is advanced to the region of interest within body 16 while "proximal" refers to the opposite end of the catheter 18, 20, 22 that is disposed outside of the body and manipulated by manually by a clinician or automatically through, for example, robotic controls. The catheters 18, 20, 22 may be inserted within a vessel located near the surface of body 16 (e.g., in an artery or vein in the leg, neck, or arm) in a conventional manner and maneuvered to a region of interest in body 16 such as heart 12.

Figure 2:
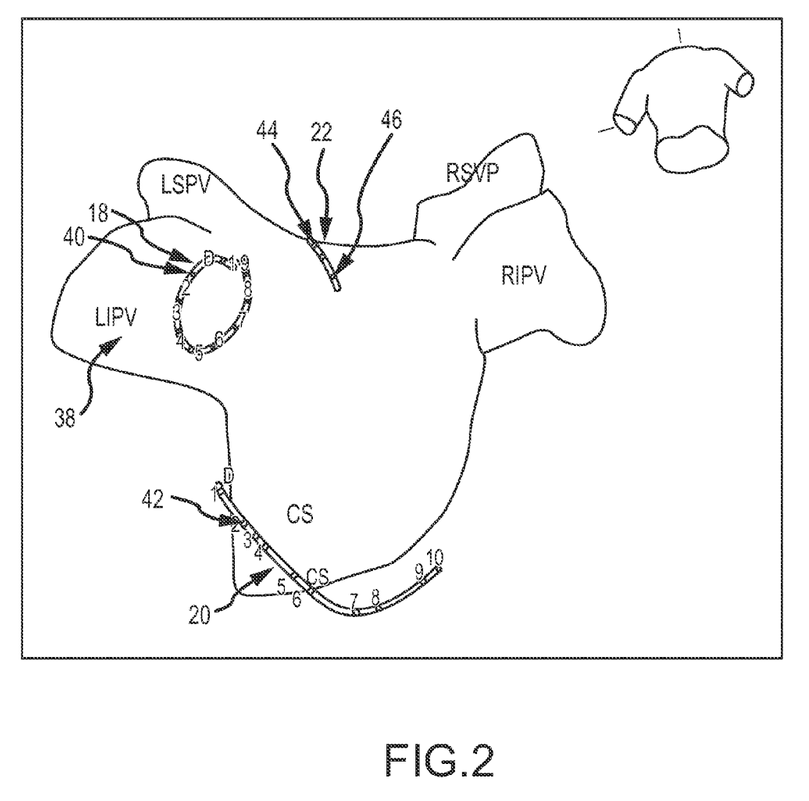
FIG. 2 is a representative view of an image showing an anatomical map of the left atrium and catheters in use during an ablation procedure.

EP catheter 18 is provided for use in gathering EP data associated with heart 12 to enable generation of an image of the geometry of the heart surface and related EP data. Referring to FIG. 2, in the illustrated embodiment, EP catheter 18 comprises a circular or spiral mapping catheter in which the distal end of catheter 18 may be configured or deformed to engage the surface of an annular member such as a pulmonary vein 38. Catheter 18 includes a plurality of position sensors 40 that are configured to contact portions of tissue in heart 12. In the illustrated embodiment, positions sensors 40 comprise electrodes. Sensors 40 are placed within electrical fields created in body 16 (e.g., within the heart 12) by exciting patch electrodes 14. Sensors 40 experience voltages that are dependent on the location between the patch electrodes 14 and the position of the sensors 40 relative to the surface of heart 12. Voltage measurement comparisons made between sensors 40 can be used to determine the position of the sensors 40 within heart 12. Movement of the sensors 40 within heart 12 (e.g., within a heart chamber) produces information regarding the geometry of the heart 12 as well as EP data. For example, voltage levels on the tissue surface over time may be projected on the image of the geometry of the heart 12 as an electrical activation map. The voltage levels may be represented in various colors and the EP data may be animated to show the passage of electromagnetic waves over the tissue surface. Information received from the sensors 40 can also be used to display the location and orientation of the sensors 40 and/or the tip of EP catheter 18 within heart 12. In accordance with various embodiments of systems and method in accordance with the present teachings described below, catheter 18 also provides a means for assessing electrical conductivity of tissues such as those in pulmonary vein 38 and for assessing blood flow velocity through the mitral valve of heart 12 and movement of the portion of the myocardium making up the mitral annulus.

Coronary sinus (CS) catheter 20 may also be provided for use in gathering EP data associated with heart 12 to enable generation of an image of the geometry of the heart surface and related EP data. Because the coronary sinus is a relatively stable location, catheter 20 may also provide a positional reference against which positions measurements for catheters 18, 22 are compared to compensate for cardiac motion. In accordance with one embodiment of a system and method in accordance with the present teachings, catheter 20 also provides a means for assessing blood flow velocity through the mitral valve of heart 12 and movement of the portion of the myocardium making up the mitral annulus. Like catheter 18, catheter 20 may include a plurality of positions sensors 42 that are configured to contact portions of tissue in heart 12 (and particularly portions of the coronary sinus). Sensors 42 may again comprise electrodes and may operate in a manner similar to sensors 40 on catheter 18.

Ablation catheter 22 is provided for examination, diagnosis and treatment of tissues within heart 12 and, in particular, to deliver ablation energy to selected tissue within heart 12 for the purpose of short-circuiting or open-circuiting stray electrical pathways in heart 12 as in interrupting a reentrant circuit with a lesion transaction the pathway. In the illustrated embodiment, catheter 22 is a radio-frequency (RF) ablation catheter having a tip electrode 44 at a distal end configured to deliver RF energy to ablate tissue. It should be understood, however, that catheter 22 may alternatively be configured to deliver any of a variety of conventional ablation energies including ultrasound, light based energies (e.g., laser) or thermal energies (e.g., cryoablation). Catheter 22 may connected to a fluid source having a biocompatible fluid such as saline through a pump for irrigation. Catheter 22 is also electrically connected to ablation generator 24 for delivery of RF energy. Catheter 22 may include a cable connector or interface, a handle, a shaft having a proximal end and a distal end on which electrode 44 is supported. Catheter 22 may also include one or more position sensors 46 which may take the form of ring electrodes in the illustrated embodiment. Position sensors 46 may again operate in a manner similar to sensors 40 on catheter 18. Catheter 22 may also include other conventional components not illustrated herein such as a temperature sensor, additional electrodes for electrophysiological studies, catheter identification and location, pacing, cardiac mapping and ablation, and corresponding conductors or leads.

As noted above, position sensors 40, 42, 46 comprise electrodes in the illustrated embodiment that are configured to generate an induced voltage in the presence of an electrical field generated by patch electrodes 14. It should be understood, however, that other conventional position and navigation systems could be employed including, for example, magnetic position and navigation systems such as the system offered for sale by Mediguide Ltd. under the trademark "GMPS." In this type of system, the positions sensors on each of catheters 18, 20, 22 may comprise coils or other conductors in which an induced current is representative of a location of the position sensor in a magnetic field. The magnetic field may be generated by a conventional magnetic field generator including, for example, three coils, arranged to create a magnetic field in and around heart 12. The magnetic field generator may be located above or below the patient (e.g., under a patient table) or in another appropriate location.

Ablation generator 24 generates, delivers and controls RF energy used by ablation catheter 22. Generator 24 is conventional in the art and may comprise the commercially available unit sold under the model number IBI-1500T RF Cardiac Ablation Generator, available from Irvine Biomedical, Inc. Generator 24 includes an RF ablation signal source configured to generate an ablation signal that is output across a pair of source connectors: a positive polarity connector which may connect to tip electrode 44; and a negative polarity connector which may be electrically connected by conductors or lead wires to one of patch electrodes 14 and/or other patch electrodes (not shown) to avoid interrupting the electrical navigation signals during ablation energy delivery. It should be understood that the term connectors as used herein does not imply a particular type of physical interface mechanism, but is rather broadly contemplated to represent one or more electrical nodes. The signal source is configured to generate a signal at a predetermined frequency in accordance with one or more user specified parameters (e.g., power, time, etc.) and under the control of various feedback sensing and control circuitry as is know in the art. The signal source may generate a signal, for example, with a frequency of about 450 kHz or greater. Generator 24 may also monitor various parameters associated with the ablation procedure including impedance, the temperature at the tip of the catheter, ablation energy and the position of the catheter and provide feedback to the clinician regarding these parameters.

EP monitor 26 is provided to display electrophysiology data including, for example, an electrogram. Monitor 26 is conventional in the art and may comprise an LCD or CRT monitor or another conventional monitor. Monitor 26 may receive inputs from ablation generator 24 as well as other conventional EP lab components not shown in the illustrated embodiment.

Electronic control unit (ECU) 28 provides a means for controlling the operation of various components of system 10 including catheters 18, 20, 22, ablation generator 24, and switch 36. ECU 28 also provides a means for determining the geometry of heart 12, EP characteristics of heart 12 and the position and orientation of catheters 18, 20, 22. ECU 28 also provides a means for generating display signals used to control display 30. ECU 28 may comprise a programmable microprocessor or microcontroller or may comprise an application specific integrated circuit (ASIC). ECU 28 may include a central processing unit (CPU) and an input/output (I/O) interface through which ECU 28 may receive a plurality of input signals including signals generated by patch electrodes 14, catheters 18, 20, 22 and position sensors 40, 42, 46, respectively, located on catheters 18, 20, 22 and generate a plurality of output signals including those used to control and/or provide data to catheters 18, 20, 22, ablation generators 24, display 30, and switch 36.

Figure 3A:
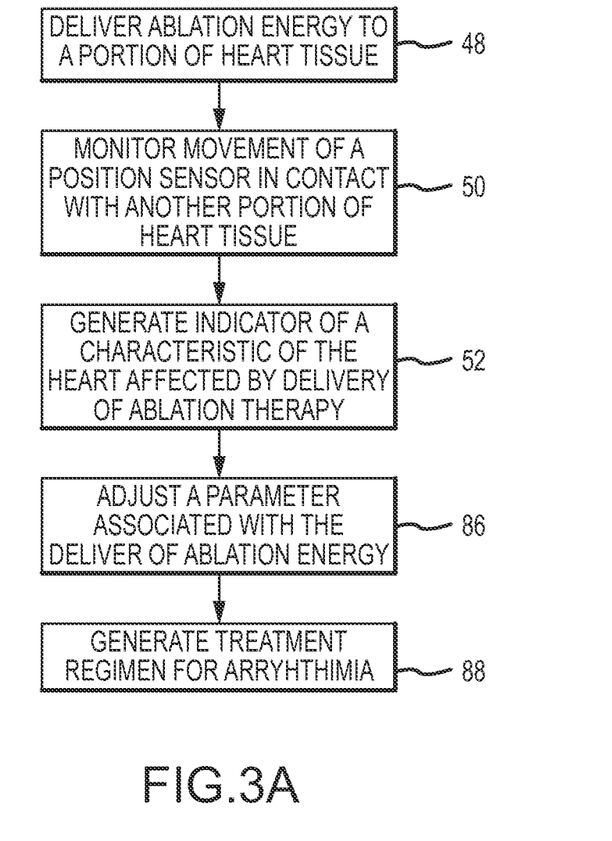
FIGS. 3A-B are a flow chart diagrams illustrating various embodiments of a method for treating a arrhythmia of the heart in accordance with the present teachings.

In accordance with the present invention, ECU 22 is configured with appropriate programming instructions or code (i.e., software) to perform several steps in a method for treating an arrhythmia in heart 12. Referring now to FIG. 3A, the may include the step 48 of delivering ablation energy to a portion of tissue of heart 12. ECU 28 may be configured in a conventional manner to generate control signals used to control ablation catheter 22 such that ablation catheter 22 delivers an appropriate level of ablation energy to tissue disposed proximate tip electrode 44.

The inventive method may further include the step 50 of monitoring the movement of a position sensor in contact with a portion of tissue of heart 12 (e.g., a portion of tissue other than the portion to which ablation energy is delivered), such as one of position sensors 40, 42, 46 over a period of time T. In operation, ECU 28 generates signals to control switch 36 and thereby selectively energize patch electrodes 14. ECU 28 receives position signals from EP catheter 18, coronary sinus catheter 20 and ablation catheter 22, and particularly position sensors 40, 42, 46, respectively, reflecting changes in voltage levels on position sensors 40, 42, 46 and from the non-energized patch electrodes 14. ECU 28 uses the raw location data produced by position sensors 40, 42, 46, and electrodes 14 and corrects the data to account for respiration and other artifacts.

ECU 28 may use the information obtained in step 50 in a variety of ways. In addition to using the information in the embodiments of the systems and method described below, ECU 28 may, for example, use the information generated by positions sensors 42 on EP catheter 18 to generate display signals to create an electrophysiological map of heart 12. ECU 28 may use the information generated by position sensors 46 on ablation catheter 22 to generate display signals illustrating the position of catheter 22 relative to an image of heart 12. Where position sensors 40, 42, 46 are in contact with tissue of heart 12, such as position sensors 40 of EP catheter 18 and position sensors 42 of coronary sinus catheter 20, the information obtained from position sensors 40, 42, 46 is indicative of the motion or movement of those portions of tissue. Therefore, ECU 28 may also use the information generated by position sensors 40, 42, 46, to generate display signals to create a motion map of heart 12. ECU 28 determines the velocities (i.e., speed and direction) of individual sensors 40, 42, 46, and projects the velocities onto tomographic planes such as those conventionally used in echocardiographic imaging including long-axis and short-axis planes. In this manner, the motion map created by ECU 28 is able to provide information typically obtained through echocardiography imaging and avoids the cost and risk associated with the introduction of an intracardiac echocardiograph (ICE) catheter and required personnel. The motion map may comprise a local motion map reflecting the movement of one or more position sensors 40, 42, 46 in a region of heart 12 or a global motion map reflected in, for example, a three dimensional anatomical map showing changes to the geometry of heart 12 during the cardiac cycle and/or during delivery of ablation therapy. ECU 28 may also use the information to generate contractility or volumetric indices including, for example, peak velocity of one or more sensors 40, 42, 46 to indicate how quickly or forcefully heart 12 is contracting, peak excursion (distance) (absolute or along a tomographic direction such as radial) of sensors 40, 42, 46 in contact with heart 12 to indicate an amount of ejection, changes in position of sensors 40, 42, 46 or distance between sensors 40, 42, 46 at points in time gated to end diastole and/or end systole to estimate heart chamber dimension, chamber volume, stroke volume and/or ejection fraction, and indices of synchrony or dyssyncrony derived from correlation or coordination of motion among multiple sensors 40, 42, 46 in contact with heart 12.

The method may continue with the step 52 generating an indicator of a characteristic of heart 12 affected by delivery of ablation energy in response to the movement of one or more position sensors 40, 42, 46 over the period of time T. Ablation therapy can affect a wide variety of characteristics of heart 12. For example, ablation therapy is intended to short circuit stray electrical pathways. Accordingly, in one embodiment discussed in greater detail below, the indicated characteristic may comprise electrical conductivity in a portion of tissue in heart 12. Ablation therapy can also cause changes in the hemodynamic operation of heart 12. Accordingly, in other embodiments discussed in greater detail below, the indicated characteristic may be blood flow velocity in a region of heart 12 or simply mechanical motion of a portion of tissue of heart 12. Ablation therapy can also changes to blood within heart 12 including cavitation (the formation of low pressure bubbles) and the creation of a thrombus. Accordingly, in other embodiments discussed in greater detail below, the indicated characteristics may be cavitation of the blood within heart 12 or the creation of a thrombus in the blood of heart 12. Likewise, the indicators used to indicate these characteristics may vary. The indicator may, for example, comprise an index value indicative of the characteristic. The indicator may alternatively comprise, for example, image data configured to cause a display such as display 30 to generate an image of heart 12 (e.g., a motion map). The indicator may also be used in a variety of ways. The indicator may provide a visual representation of the characteristic to the clinician in order to allow the clinician to assess the patient and the effectiveness of the therapy and to make further diagnostic and treatment decisions. The indicator may also be used by ECU 28 as a feedback control for ablation generator 22 or other components of system 10.

Figure 3B:
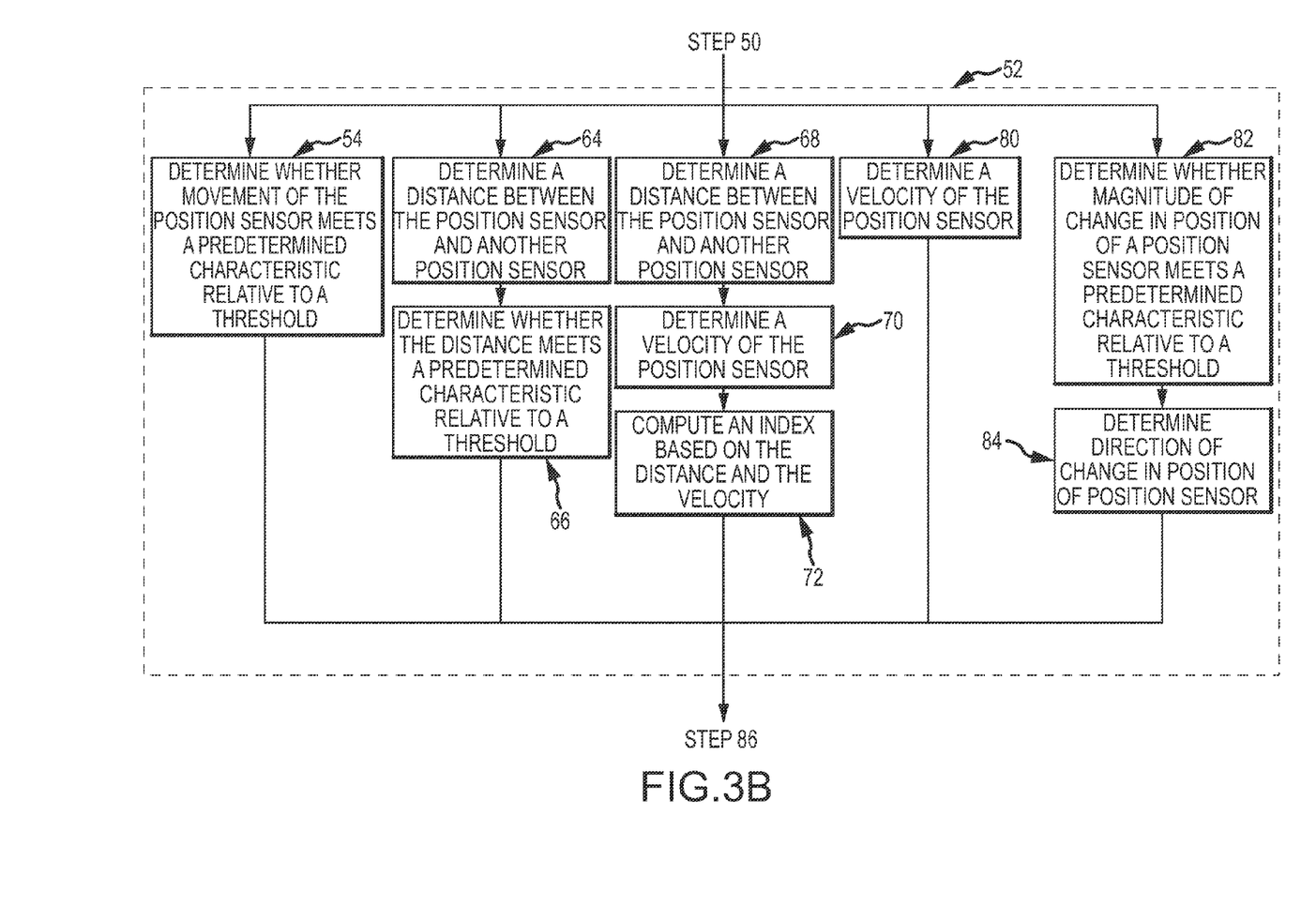
Figure 4:
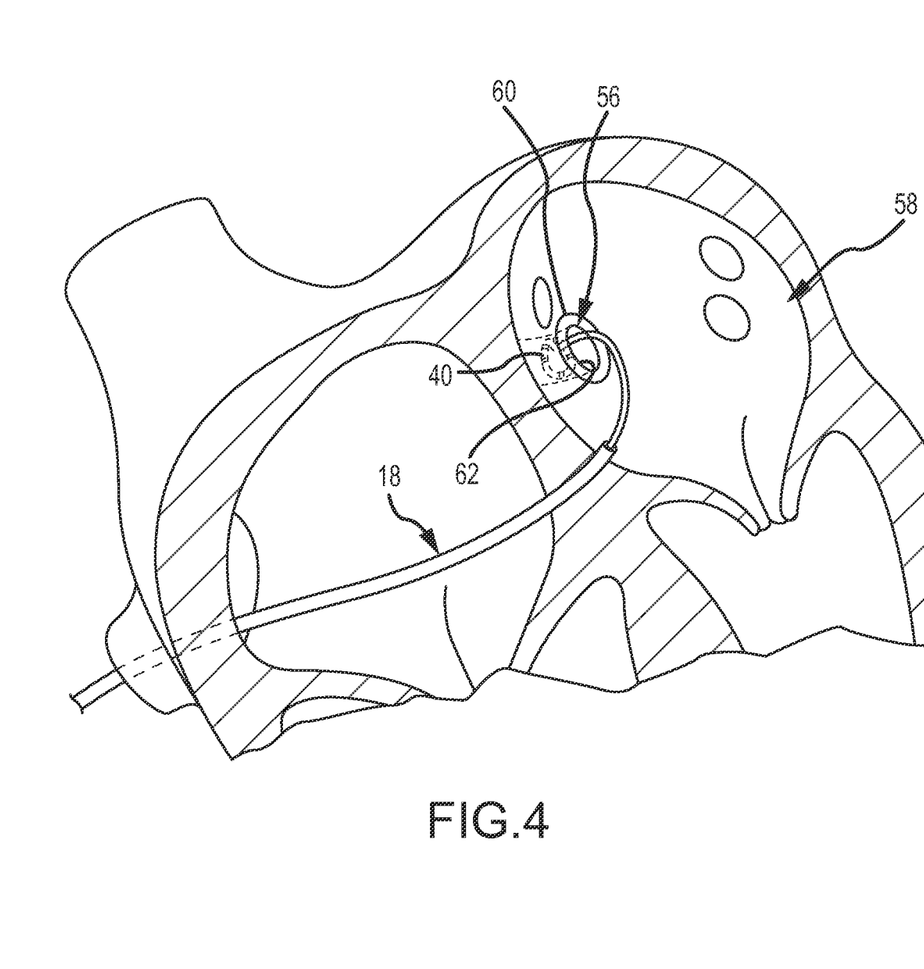
FIG. 4 is a perspective view of a pulmonary vein with a distal portion of a catheter having a plurality of position sensors disposed distally of the ostium of the pulmonary vein.

In one embodiment of a system and method in accordance with the present teachings, the presence or absence of electrical activation at, and/or the electrical conductivity of, a portion of tissue affected by the delivery of ablation therapy is measured and an appropriate indicator of this characteristic is generated. Referring to FIG. 3B, step 52 may include the substep 54 of determining whether the movement of the position sensor or sensors 40, 42, 46 over the period of time T meets a predetermined characteristic relative to a predetermined threshold. For example, ECU 28 may be configured to determine whether the distance moved by a given sensor 40, 42, 46 is less than a predetermined threshold value so as to indicate a lack of local electrical activation and/or that there is minimal or no electrical conductivity in certain tissue within heart 12. Referring to FIG. 4, a common treatment for atrial fibrillation involves isolation of the pulmonary veins 56 to terminate electrical pathways from the pulmonary veins 56 to the left atrium 58.

Towards this end, ablation catheter 22 may create a circumferential line of ablation 60 near the ostium 62 of each pulmonary vein 56. EP catheter 18 may be placed within the pulmonary vein 56 distally of the ostium 62 and the line of ablation 60. The position of position sensors 40 may be monitored over a period of time encompassing periods before, during and after ablation is performed near the ostium 62. Prior to the delivery of ablation energy, the tissue with which position sensors 40 are in contact will exhibit at least some movement. If the ablation near the ostium 62 is successfully carried out, however, the electrical pathway between the pulmonary vein 56 and the left atrium 58 should be severed thereby eliminating or reducing motion of the tissue in pulmonary vein 56 distal of the ostium 62. Position sensors 40 in contact with this tissue will therefore indicate a relatively constant output (corrected for general patient and respiratory movement) indicative of a lack of motion during the cardiac cycle. ECU 28 may determine whether the movement of sensors 40 is less than a threshold amount and provide an indicator of the electrical conductivity in the tissue.

As an alternative to comparing the movement of an individual sensor, a similar result may be obtained by comparing the movement of the sensor relative to another sensor. Referring again to FIG. 3B, therefore, in an alternative embodiment, step 52 may include the substeps 64, 66 of determining a distance between a position sensor 40 and another position sensor over the period of time T and determining whether the distance meets a predetermined characteristic relative to a predetermined threshold. Referring to FIG. 4, for example, ECU 28 may determine the distance between a sensor 40 in pulmonary vein 56 and another position sensor such as sensor 46 on catheter 22 over the period of time T. During ablation of the area around the ostium 62, the position of sensor 40 relative to a position sensor 46 on catheter 22 (FIG. 2) should vary over time. Following a successful ablation, however, the position of sensor 40 on EP catheter 18 should remain relatively constant given the lack of electrical activity in the tissue contacted by sensor 40. Similarly, the distance between the sensor 40 and sensor 46 on ablation catheter 22 should remain either constant or change less than prior to the ablation. ECU 28 can compare the distance between the two sensors 40, 46 over time T against a predetermined threshold. For example, ECU 28 may determine whether the distance is less than a threshold amount (including one derived from movement of the sensor 40 prior to ablation) indicative of a lack of motion and, therefore, electrical conductivity.

It should be understood that many aspects of the embodiment illustrated in FIG. 4 are exemplary only. For example, the same principles may be used to evaluate the electrical conductivity of other tissues in heart 12 depending on the arrhythmia being treated and the resulting ablation therapy applied to treat that arrhythmia. For example, treatment of atrial flutter often involves ablation of the cavotriscuspid isthmus. EP catheter 18 can be positioned at various locations (e.g., on one side of an ablation line or along the septal isthmus) where electrical conductivity, and the resultant motion, is expected to end following successful ablation therapy.

In another embodiment of a system and method in accordance with the present teachings, the blood flow velocity within heart 12 affected by the delivery of ablation therapy is measured and an appropriate indicator of this characteristic is generated. Referring again to FIG. 3B, step 52 may include several substeps 68, 70, 72. In substep 68, ECU 28 determines the distance between a pair of position sensors over a period of time. The position sensors may be disposed at locations such that the distance between the two sensors is indicative of the size of an opening through which blood flows and, therefore, blood flow velocity. In substep 70, ECU determines a velocity of one of the positions sensors over the period of time T. The position sensor may be disposed at a location such that the velocity of the sensor is indicative of motion (i.e., expansion and contraction) of the tissue through which blood flows and, therefore, blood flow velocity. In substep 72, ECU may compute an index responsive to the distance and the velocity that is also indicative of blood flow velocity.

Figure 5:
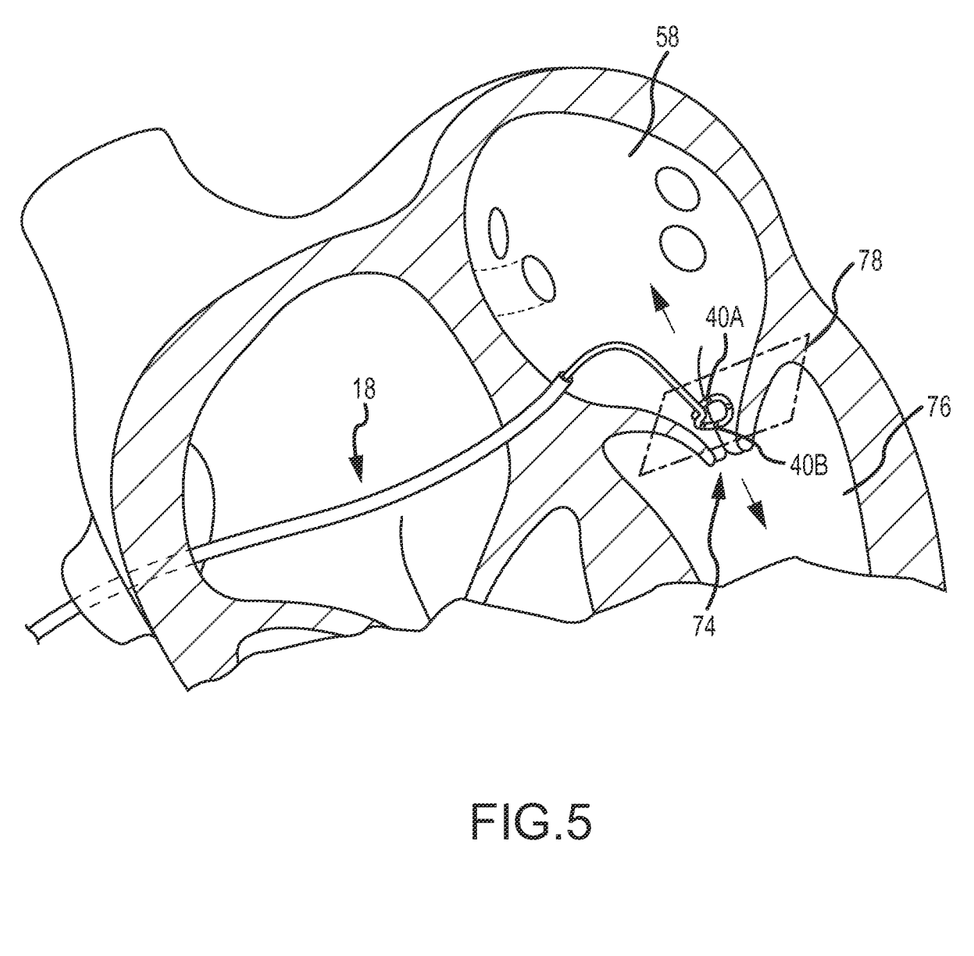
FIG. 5 is a perspective view of a mitral valve with a distal portion of a catheter having a plurality of position sensors placed in the mitral valve annulus.

Referring to FIG. 5, in one embodiment the blood flow velocity through the mitral valve 74 is measured to evaluate the contribution of the left atrium 58 to the filling of the left ventricle 76. One risk associated with atrial ablation is a decrease in regional wall motion. By severing certain electrical pathways and, as a result, diminishing the motion of heart 12, ablation therapy may reduce the flow of blood through regions of heart 12 leading to stagnation and coagulation of the blood and to potential thrombus. The thrombus can dislodge and enter the circulation system, leading to a myocardium infarction, stroke, or blockage of blood flow to various vital organs. One area in which blood may collect is the left atrium appendage or behind mitral valve leaflets. Coagulation of the blood may lead to production of a thrombus in the left atrium 58. EP catheter 18 may be positioned in the mitral valve annulus to measure movement of the surrounding tissue and this information may be used by ECU 28 to generate an indicator of the affect of ablation therapy on blood flow velocity through mitral valve 74. In the illustrated embodiment, catheter 18 includes a plurality of position sensors 40 arranged in contact with tissue along the inner diameter of the mitral valve in annular plane 78. The movement of sensors 40 before, during, and after ablation therapy may be monitored as described hereinabove. Using the information provided by sensors 40, ECU 28 may be configured to determine a distance between a pair of sensors 40, such as diametrically opposite sensors 40A, 40B. The change in distance will provide an indication of blood flow velocity through the mitral valve 74. In particular, an increase in distance is indicative of increased flow velocity while a decrease in distance is indicative of decreased flow velocity. ECU 28 may also be configured to determine a velocity of one or more of sensors 40 using the position information from a given sensor over a period of time T. The velocity of a given sensor 40 in a direction perpendicular to plane 78 is indicative of the tissue velocity and, in particular, the velocity of the myocardium making up the mitral annulus. ECU 28 may further be configured to compute an index responsive to the determined distance and velocity. In particular, the ratio between the change in distance between sensors 40 in plane 78 of the mitral valve 74 (i.e. change in blood flow through the mitral valve 74) and the velocity of the sensors 40 perpendicular to plane 78 (i.e. the velocity of the myocardium) is analogous to the well-known E/E' ratio (efficiency of early filing (E) relative to early diastolic mitral annular velocity (E')) derived from tissue Doppler imaging.

It should again be understood that many aspects of the above-described and illustrated embodiment are exemplary only. For example, although EP catheter 18 is used in the embodiment illustrated in FIG. 5, coronary sinus catheter 20 may alternatively be used to obtain similar measurements. Catheter 20 is typically positioned such that some position sensors 42 are located at the left ventricle basal plane near the mitral valve 74 and can therefore function in a similar manner. Further, although the velocity of the sensors 40 is used together with the distance between sensors 40 to generate an index indicative of blood flow velocity, it should be understood that the velocity of sensors 40 alone is indicative of another characteristic of heart 12, tissue motion, affected by the delivery of ablation energy. Referring to FIG. 3B, therefore, in another embodiment of a method in accordance with the present teachings, step 52 includes the substep 80 of determining a velocity of a position sensor, such as position sensor 40, over a period of time T. ECU 28 may monitor the movement of one or more position sensors 40, 42, 46 in a region of interest in heart 12 and use this information to calculate regional tissue velocities in heart 12 and generate an indicator in the form of an index indicative of the regional tissue velocity. Monitoring the velocities of multiple sensors 40, 42, 46 in close proximity to one another permits an estimate of local strain to be determined from the differential motion of the sensors 40, 42, 46 divided by the distance separating the sensors 40, 42, 46 or by integrating the differential velocities divided by the distance separating the sensors 40, 42, 46 over a short period of time such as during active systole or diastole. An index of strain, such as peak strain, minimum strain, median strain, mean strain, $90^{th}$ percentile of strain, etc., among measured local strains in a region or chamber of heart 12 may be generated by ECU 28 and used to determine whether the tissue in heart 12 is actively contracting in order to determine an appropriate anticoagulation therapy.

In yet another embodiment of a system and method in accordance with the present teachings, cavitation and/or thrombus formation in the blood of heart 12 resulting from the delivery of ablation therapy is measured and an appropriate indicator of this characteristic is generated. One risk associated with ablation therapy, particularly when radio-frequency energy is used as the ablation energy, is cavitation in the blood (i.e., the formation of low pressure bubbles within the blood) as the blood is heated. These bubbles create the risk of an embolism—particularly if they travel to cerebral or coronary arteries. Another risk associated with ablation therapy is thrombus formation from coagulation of the blood due to the use of a foreign body (i.e., the ablation catheter 22) in the blood. Both cavitation of the blood and the formation of a thrombus impact the local electrical field within heart 12 and will affect the output of position sensors 40, 42, 46. In particular, cavitation increases local impedance and causes a change in output in one or more of sensors 40, 42, 46, such that the sensors 40, 42, 46, appear to move away from a bubble. A thrombus decreases local impedance and causes a change in output in one or more of sensors 40, 42, 46, such that the sensors 40, 42, 46, appear to move toward the thrombus. ECU 28 detects this change in position and may generate an indicator indicative of cavitation or thrombus formation in the blood. Referring again to FIG. 3B step 52 may include the substep 82 of determining whether a magnitude of a change in position of one or more sensors 40, 42, 46, meets a predetermined characteristic relative to a predetermined threshold value. For example, in one embodiment ECU 28 may determine whether the magnitude of the change in position is greater than or equal to the threshold and, if so, generates an indicator of this fact such as a numerical value or an alarm (e.g. an audio or visual alarm). Step 52 may further include the substeps of incrementing a counter in a memory of ECU 28 if the predetermined condition is met and generating the indicator only when the counter reaches a predetermined number. Step 52 may also include the substep 84 of determining the direction of the change in position of the one or more sensors 40, 42, 45. As noted above, the direction of the change in position may be used by ECU 28 to determine whether the change in position reflects the presence of cavitation or a thrombus.

In each of the embodiments described hereinabove, the relative movement of one or more position sensors 40, 42, 46 on a particular catheter such as EP catheter 18 or coronary sinus catheter 20 is used to generate an indicator of a characteristic of heart 12 affected by the delivery ablation energy. It should be understood, however, that the movement of position sensors 40, 42, 46 on multiple catheters (e.g., sensors 40, 42 on EP catheter 18 and coronary sinus catheter 20) could be used in the generate the indicator of a given characteristic. It should also be understood that ECU 28 may generate multiple indicators for a given characteristic (e.g. both image data and an index value) and may generate indicators for multiple characteristics simultaneously.

Referring again to FIG. 3A, the method may further include the step 86 of adjusting a parameter associated with the delivery of ablation energy responsive to the indicator. In this manner, the indicator generated based on the movement of position sensors 40, 42, 46 may be used as a feedback for the control of ablation catheter 22. ECU 28 may generate control signals for catheter 22 responsive to the generated indicator. These control signals may result in adjustment of a variety of parameters including, for example, the duration of delivery or duty cycle of ablation energy to a particular site in heart 12, the intensity of the ablation energy, and/or an irrigation flow rate. In this manner, a clinician can adjust the ablation procedure in real time to, for example, move to a more aggressive therapeutic approach (e.g., moving from dominant-frequency based targeting to complete isolation) or to change the approach (e.g., by moving from a typical atrial fibrillation ablation strategy to AV-nodal ablation in preparation for implanting a pacemaker).

The method may also include the step 88 of generating a treatment regimen for the arrhythmia responsive to the indicator. As noted hereinabove, there are a number of risks associated with ablation therapy including a decrease in regional wall motion within heart 12, cavitation of the blood within heart 12 and coagulation of the blood resulting from the presence of the ablation catheter 22. It is desirable to be able to assess these risks and minimize or eliminate the risks through proper treatment both during ablation and afterwards. ECU 28 may generate indicators that are indicative of effects from ablation therapy that are themselves indicative of the above-recited risks including tissue motion, blood flow velocity and/or changes in the blood. Depending on the value of the indicator, ECU 28 may generate recommendations for further treatment. In one embodiment of the invention, step 88 may includes the substeps of determining whether the indicator meets a predetermined characteristic relative to a predetermined threshold value and of generating a predetermined treatment regimen if the indicator meets that characteristic. For example, if the indicator indicates that regional tissue motion is below a threshold or that blood flow velocity is too low, ECU 28 may recommend a treatment regimen with drugs or other mechanisms for increased anticoagulation of the blood. The treatment regimen may, for example, be in the form of textual instructions displayed on display 30, downloaded to a portable storage medium, transmitted to another computing device through a telecommunications network, or printed out on an accessory device.

Display 30 is provided to convey information to a clinician to assist in diagnosis and treatment. Display 30 may comprise a conventional computer monitor or other display device. Display 30 presents a graphical user interface (GUI) to the physician. The GUI may include a variety of information including, for example, an image of the geometry of heart 12, EP data associated with heart 12, graphs illustrating voltage levels over time for various electrodes, and images of catheters 18, 20, 22. Examples of the type of information that may be displayed are shown in commonly assigned U.S. Pat. No. 7,263,397, the entire disclosure of which is incorporated herein by reference.

A system and method for treating an arrhythmia in a heart in accordance with the present teachings is advantageous because the system and method provide an effective measure of the effectiveness and safety of ablation therapy. In particular, the motion of the position sensors is used to infer motion of the cardiac tissue and this motion is used to assess the impact of ablation therapy on a variety of characteristics associated with the heart, including tissue motion, blood flow velocity, electrical conductivity and changes to the blood, that are affected by ablation therapy and are indicative of the success or failure of that therapy and risks associated with that therapy. The inventive system and method therefore enable a clinician to better assess the efficacy and safety of ablation therapy.

Although several embodiments of this invention have been described above with a certain degree of particularity, those skilled in the art could make numerous alterations to the disclosed embodiments without departing from the scope of this invention. All directional references (e.g., upper, lower, upward, downward, left, right, leftward, rightward, top, bottom, above, below, vertical, horizontal, clockwise and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the invention as defined in the appended claims.

What is claimed is:

1. A system for treating an arrhythmia in a heart, comprising:
an electronic control unit configured to:
monitor movement of a first portion of tissue of said heart by determining a distance between a first position sensor and a second position sensor over a period of time;
generate a characteristic indicator signal by comparing said movement of said first position sensor over said period of time to a predetermined threshold value of tissue movement, said characteristic indicator signal being representative of a characteristic of said heart at said first portion of tissue of said heart affected by delivery of ablation energy to a second portion of said tissue of said heart from an ablation catheter, wherein said characteristic indicator signal is configured to generate an indicator and wherein said characteristic comprises electrical conductivity in the first portion of said tissue in said heart;
determine a velocity of said first position sensor over said period of time and to compute an index responsive to said distance and said velocity; and generate a control signal for controlling the ablation catheter responsive to said characteristic indicator signal, said control signal adjusting a parameter associated with the delivery of said ablation energy.

2. The system of claim 1 wherein said parameter comprises one of a duration of said delivery of said ablation energy, a duty cycle of said delivery of said ablation energy, an intensity of said ablation energy, and an irrigation flow rate.

3. The system of claim 1 wherein said electronic control unit is further configured to monitor movement of the second position sensor indicative of movement of said second portion of said tissue of said heart over said period of time, and to generate a second characteristic indicator signal responsive to said movement of said first position sensor and said movement of said second position sensor over said period of time of said characteristic of said heart affected by said delivery of said ablation energy to said tissue of said heart.

4. The system of claim 3, wherein said characteristic comprises a first tissue strain and said second characteristic comprises a second tissue strain.

5. The system of claim 4, wherein said electronic control unit is further configured to determine a contraction between said first portion of said tissue and said second portion of said tissue using said first tissue strain and said second tissue strain.

6. The system of claim 1 wherein said electronic control unit is further configured, in determining said characteristic indicator signal, to determine whether said movement of said first position sensor over said period of time meets a predetermined characteristic relative to said predetermined threshold value of tissue movement.

7. The system of claim 1 wherein said electronic control unit is further configured, in determining said characteristic indicator signal, to determine whether said distance meets a predetermined characteristic relative to said predetermined threshold value of tissue movement.

8. The system of claim 1 wherein said electronic control unit is further configured, in determining said characteristic indicator signal, to determine whether a magnitude of said movement of said first position sensor meets a predetermined characteristic relative to said predetermined threshold value of tissue movement.

9. The system of claim 1 wherein said electronic control unit is further configured, in determining said characteristic indicator signal, to determine a direction of said movement of said first position sensor.

10. The system of claim 1 wherein said characteristic further comprises blood flow velocity at the first portion of said tissue in said heart.

11. The system of claim 1 wherein said indicator comprises an index value indicative of the characteristic.

12. The system of claim 1 wherein said indicator comprises image data configured to cause a display to generate an image of said tissue.

13. The system of claim 1 wherein said characteristic indicator signal is configured to generate an indicator comprising a visual representation of said characteristic.

14. A system for treating an arrhythmia in a heart, comprising:
an electronic control unit configured to:
determine a distance between a first position sensor at a first location and a second position sensor at a second location over a period of time;
determine a velocity of one or more of the first position sensor and the second position sensor over the period of time; and
compute an index based on the distance and the velocity of one or more of the first position sensor and the second position sensor.

15. The system of claim 14, where the electronic control unit is further configured to determine, using the velocity of the one or more of the first position sensor and the second position sensor, a motion of a tissue through which blood flows.

16. The system of claim 14, wherein the electronic control unit is further configured to determine, using the velocity of the one or more of the first position sensor and the second position sensor to determine a motion of the tissue through which blood flows, a blood flow velocity.

17. The system of claim 14, wherein the index is indicative of a blood flow velocity.

18. The system of claim 14, wherein the distance is indicative of a size of an opening through which blood flows which is indicative of a blood flow velocity.

* * * * *